United States Patent [19]
Prentice et al.

[11] 4,378,434
[45] Mar. 29, 1983

[54] PROCESS FOR THE PRODUCTION OF USEFUL CULTURES AND/OR METABOLITES

[75] Inventors: Robert C. Prentice, Terril; Dale W. Mastarone, Spencer, both of Iowa

[73] Assignee: Solargizer International, Inc., Bloomington, Minn.

[21] Appl. No.: 136,054

[22] Filed: Mar. 31, 1980

[51] Int. Cl.³ .......................... C12P 7/04; C12P 7/06; C12P 7/10; C12P 7/14
[52] U.S. Cl. .................................... 435/157; 435/161; 435/162; 435/165; 435/813
[58] Field of Search ............... 435/157, 161, 162, 163, 435/165, 171, 287, 293, 300, 304, 307, 310, 312, 316, 802, 813, 244, 819

[56] References Cited

U.S. PATENT DOCUMENTS

| | | | |
|---|---|---|---|
| 409,956 | 8/1889 | Gent | 435/307 X |
| 2,146,326 | 2/1939 | Bergius et al. | 435/162 |
| 2,155,134 | 4/1939 | Karsch | 435/162 |
| 2,440,925 | 5/1948 | Boeckeler | 426/13 |
| 2,450,218 | 9/1948 | Victorero | 435/310 |
| 2,451,156 | 10/1948 | De Mattos | 435/162 |
| 3,028,314 | 4/1962 | Means et al. | 435/43 |
| 3,032,476 | 5/1962 | Sher | 435/256 |
| 3,062,724 | 11/1962 | Rensser | 435/75 |
| 3,413,124 | 11/1968 | Akin | 435/313 X |
| 3,575,813 | 4/1971 | Rothmayr | 435/310 |
| 3,705,841 | 12/1972 | Lumb et al. | 435/83 |
| 3,716,375 | 2/1973 | Hancock | 435/813 X |
| 3,743,582 | 7/1973 | Kitai et al. | 435/248 |
| 3,801,468 | 4/1974 | Lumb et al. | 435/290 |
| 3,923,605 | 12/1975 | Gedde | 435/312 |
| 3,985,622 | 10/1976 | Hawkins | 435/310 |

Primary Examiner—Esther M. Kepplinger
Attorney, Agent, or Firm—Merchant, Gould, Smith, Edell, Welter & Schmidt

[57] ABSTRACT

The disclosed chemical process is carried out in a series of vertically stacked conversion (e.g. fermentation) zones which are subdivided into movable segments. Flow from one zone to another is gravity-induced. A portion of the production medium is recirculated to an upper zone, e.g. the uppermost zone, and metabolites are withdrawn from the zones. Useful metabolites include organic liquids such as alkanols made from fermentation of carbohydrate.

In apparatus (10) especially suited to the process: A generally vertically disposed fermentation tower (11) defines a generally vertically extending space containing the vertically arranged zones (15a–15h). A typical zone, e.g. zone (15c) has a floor (65c) having a drain opening (165c) for the continuous discharge by gravity of partially converted feedstock to the next lower zone (15d). Each zone (e.g. 15c) is subdivided into continuously movable segments by movable partitions (157c) for advancing the feedstock in the zone toward the drain opening. A collection means (23) disposed beneath a drain opening (165c) continuously collects a portion of the partially converted feedstock and recirculates it through a recirculation system (20) to the uppermost zone (15a). The products of the process are withdrawn by a suitable means (41) communicating with the lower end of the tower (11).

13 Claims, 7 Drawing Figures

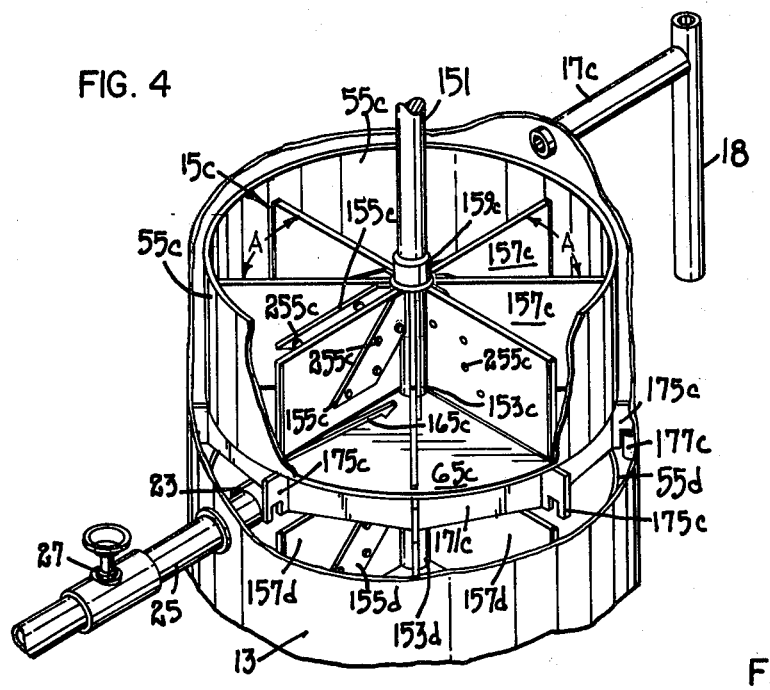
FIG. 4
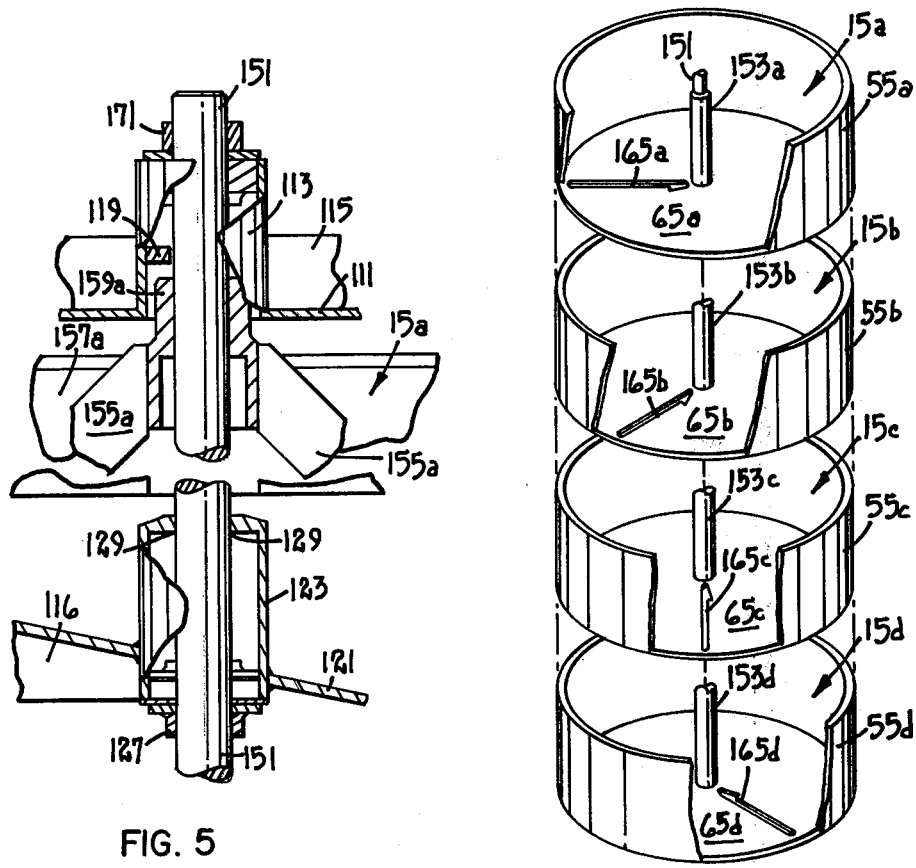
FIG. 5
FIG. 6

PROCESS FOR THE PRODUCTION OF USEFUL CULTURES AND/OR METABOLITES

CROSS REFERENCE TO RELATED APPLICATION

Copending application Ser. No. 136,053, filed of even date herewith (Mar. 31, 1980), contains a similar disclosure, and its claims are directed to technologically related subject matter.

TECHNICAL FIELD

This invention relates to a process for stimulating the growth of a microorganism culture in a series of growth zones and withdrawing metabolites produced by the culture. An aspect of this invention relates to a continuous process for the production of useful metabolites from a culture, utilizing metabolic processes of the culture. Another aspect of this invention relates to a continuous process for the production of useful metabolites (e.g. organic liquids or solids or useful gases such as carbon dioxide) from a carbohydrate-containing nutrient medium by fermentation of the medium. Still another aspect of this invention relates to the fermentation of a fermentable feedstock on a continuous basis (as opposed to a batch basis). A still further aspect of this invention relates to a process for continuously converting carbohydrate-containing materials to a "beer" comprising from 1 to about 20% by weight or by volume of an alkanol (preferably ethyl alcohol) dissolved in water.

DESCRIPTION OF THE PRIOR ART

The conversion of carbohydrate-containing materials and other fermentable feedstocks to organic liquids is one of the oldest of the chemical arts. However, the discovery that microorganisms provide the catalytic action for the conversion is a relatively recent discovery going back only to the time of Louis Pasteur. Building upon the monumental discoveries of Pasteur, chemists and microbiologists have spent many decades of effort investigating and utilizing the metabolic processes of micoorganisms for industrial applications. In some instances, recovery of the metabolites themselves is the goal, e.g. in the manufacture of alcoholic beverages, solvents, fuels, pharmaceuticals, and the like. In other cases, recovery of residues from the microorganism culture is of equal or greater importance. For example, the ultimate goal of the process may be the recovery of an enzyme secreted by the organisms during an organism growth phase, recovery of the nutrient material in an upgraded form (e.g. a form in which the protein content has been increased at the expense of the carbohydrate content), the utilization of cellular material from dead microorganisms, alone or in combination with nutrient residues, as a fertilizer or feed or human edible material, or even the harvesting of live microorganisms for use in some other process. Frequently, it is both desirable and economically essential to utilize both the metabolites produced by the culture and the nutrient residues from the culture (typically blended with killed microorganisms). The production of fuel alcohol illustrates this principle. If the residue of the process (e.g. the "bottoms" from the distillation column or other separation apparatus) were not useful, the income generated by the sale of the organic liquid fuel would not justify the diversion of, for example, raw feed or food ingredients from the stream of useful products produced by agriculture. Fortunately, a typical fermentation process for the production of food alcohol produces distillation bottoms which are useful as fertilizer, animal feed, or human-edible material.

In the ordinary industrial process in which a nutrient medium is metabolized by a microorganism culture, either an inoculum or starter culture is used, and the cells in this starter culture or inoculum are typically multiplied after the cells mature, adjust to their new environment, and obtain sufficient nutrition from the nutrient medium. (If a reduction in viscosity of the culture medium and an increase in the nutrient level relative to the microorganism population is desired, however, initial stages of production can be carried out with a deliberately imposed deficiency of nutrients.) The growth of an inoculum or starter culture into a very much larger population of microorganisms is not necessarily a smooth, easily controlled process but may instead occur in spurts or phases. The first stage of the growth of an inoculum is sometimes referred to as the initiation phase. During this phase, the cells may be generally resting or adjusting to their environment. Typically, they are not sufficiently well adjusted or sufficiently mature to achieve growth through the typical growth mechanism of binary fission. Once binary fission begins, however, the microorganism culture may pass rather rapidly into the so-called logarithmic growth phase, during which the cell population increases in accordance with a geometric progression. The logarithmic growth phase can continue more or less unhindered until the concentration of metabolites in the culture begins to reach a level which slows down or even stops further growth. This terminal phase of the growth cycle often results because of toxic effects of metabolites upon the culture. In the case of fermentation of carbohydrates with yeasts, for example, the metabolically produced ethyl alcohol is poorly tolerated by most yeasts. Some yeasts can tolerate no more than about 2% by volume of ethyl alcohol in the fermentation or production medium. Other yeasts can tolerate as much as 15% or more. Given the present state of the art, however, there are no yeasts which could tolerate the concentration of ethyl alcohol in strong alcoholic beverages (e.g. 80 U.S. proof and higher), hence the need to obtain these strong drinks by distillation.

Another factor which can contribute to the termination of the logarithmic growth phase is the exhaustion or substantial exhaustion of nutrients. This exhaustion of nutrients may be arranged for deliberately so as to stop the microbiological production process at a desired point. On the other hand, if it is desired to progress beyond this point, maintenance nutrients can be added. However, introduction of nutrients into a growth or production medium can involve risks of contamination or poisoning, introduction of extraneous microorganisms, or disruption of the environment within the growth zone (e.g. the loss of anaerobic conditions). One way of dealing with these risks and also providing optimum conditions for the logarithmic growth phase is to employ successive production units or growth zones, each zone producing metabolites (which can be withdrawn from the zone) and a harvested culture which can be used as an inoculum in the next succeeding production unit in the series. See, for example, U.S. Pat. No. 3,699,840 (Hatcher), issued June 13, 1972. The use of a multiplicity of growth zones does not, however, eliminate the need for caution in transferring the harvested culture from one zone to another. Some cultures are too delicate to be simply pumped from one tank to another without disturbing the logarithmic growth phase. In addition, if contamination of a growth zone occurs, the disruption of the entire production process could be even greater than might be the case for a single, batch-type fermentor.

Accordingly, there is still room for improvement in the design of processes for stimulating the growth of a microorganism culture or for producing useful metabolites from a culture. This invention contemplates a process which will continually bring both fresh and partly metabolized nutrient material into contact with a microorganism culture which is in the logarithmic growth phase, whereby the ratio of live, mature, rapidly growing, metabolite-tolerant microorganisms to nutrient material is generally maintained at an optimally high level, thereby increasing production through shortening of lag times, initiation and other relatively dormant phases, environmental adjustment, and exhaustion of nutrients or other conditions which may force the culture into a terminal growth phase. This invention also contemplates a process for stimulating the growth of a microorganism culture and for recovering useful metabolites which can be carried out generally continuously. Some microorganism cultures (e.g. those used to produce citric acid) tend to form a solid or semi-solid structure which facilitates continuous addition of nutrients and continuous withdrawal and recovery of the citric acid. Ordinarily, special conditions or manipulative steps are necessary to accomplish the same degree of continuous production with microorganisms which are normally kept suspended or dispersed in the nutrient medium.

SUMMARY OF THE INVENTION

Briefly, this invention relates to a process for stimulating the growth of a microorganism culture in a series of growth zones and withdrawing metabolites produced by the culture from one or more of these growth zones. When the metabolites are useful, e.g. in a continuous process for the production of oxygen-containing aliphatic compounds from a carbohydrate-containing nutrient medium by fermentation of the medium, these metabolites can be recovered. In one aspect, this invention involves:

(a) introducing a micoorganism culture comprising an inoculum and a liquid nutrient medium to the upper end of a tower-like production unit divided into a generally vertical series of tray-like growth zones, whereby the culture is introduced to the uppermost of the tray-like growth zones, each growth zone having a drain opening and being subdivided into continuously moving segments for continuously agitating the thus-introduced culture in the zone and for advancing the culture toward the drain opening;

(b) in one of these movable segments, advancing the culture toward the drain opening in the uppermost of the tray-like zones;

(c) obtaining gravity flow of the culture through the drain opening into a movable segment of the next lowest or next-to-uppermost of the tray-like growth zones;

(d) repeating steps (b) and (c) in this next-to-uppermost of the tray-like growth zones, thereby obtaining gravity flow to a movable segment of the next lowest tray-like growth zone below the aforementioned next-to-uppermost tray-like growth zone;

(e) further repeating steps (b) and (c) in successively lower tray-like growth zones until substantial multiplication of the microorganisms in the culture has been obtained (e.g. the culture has been brought to a sustained logarithmic growth phase);

(f) withdrawing a portion of the culture (including the rapidly-multiplying microorganisms and the partially metabolized nutrient medium) from one of the relatively lower tray-like growth zones and gently circulating the thus-withdrawn portion to a higher tray-like growth zone; and (g) withdrawing metabolites from at least one of the tray-like growth zones and preferably recovering the metabolite, which will typically have utility in the fuel, solvent, beverage, or pharmaceutical industries.

The foregoing process can be carried out continuously in a tower-like production unit or fermentor which is sealed off from the ambient atmosphere. Except for the transfer of highly active culture from one of the lower growth zones to a higher growth zone (preferably the uppermost growth zone), virtually all of the movement of the culture during the initial and logarithmic growth phases (approaching or even very slightly beyond any terminal growth phase) can be gravity-induced. A preferred microorganism growth culture comprises brewer's yeast and a hydrolyzed starch-containing aqueous nutrient medium. By the process of this invention, this culture can be re-used in the process at least once, typically more than once, because of the gentle treatment of the culture, the continuous replenishment of nutrients to the production medium or broth, and the withdrawal and recirculation of a portion of the culture before this portion enters the terminal growth phase.

BRIEF DESCRIPTION OF THE DRAWING

In the Drawing, wherein like numerals denote like parts in the various views,

FIG. 4 is a fragmentary perspective view of the conversion or fermentation tower, with portions broken away to show the internal structure of a tray-like conversion or fermentation or growth zone and its movable partitions or vanes;

FIG. 5 is an enlarged fragmentary view of top and bottom seal and bearing housings of the conversion or fermentation apparatus of FIG. 1, with parts broken away to show the internal structure within these housings;

FIG. 6 is a fragmentary perspective view, on a reduced scale, of the arrangement of tray-like conversion or fermentation or growth zones, with the movable partitions removed and parts broken away to illustrate the location of drain openings in the various zones.

DETAILED DESCRIPTION

Figure 1:
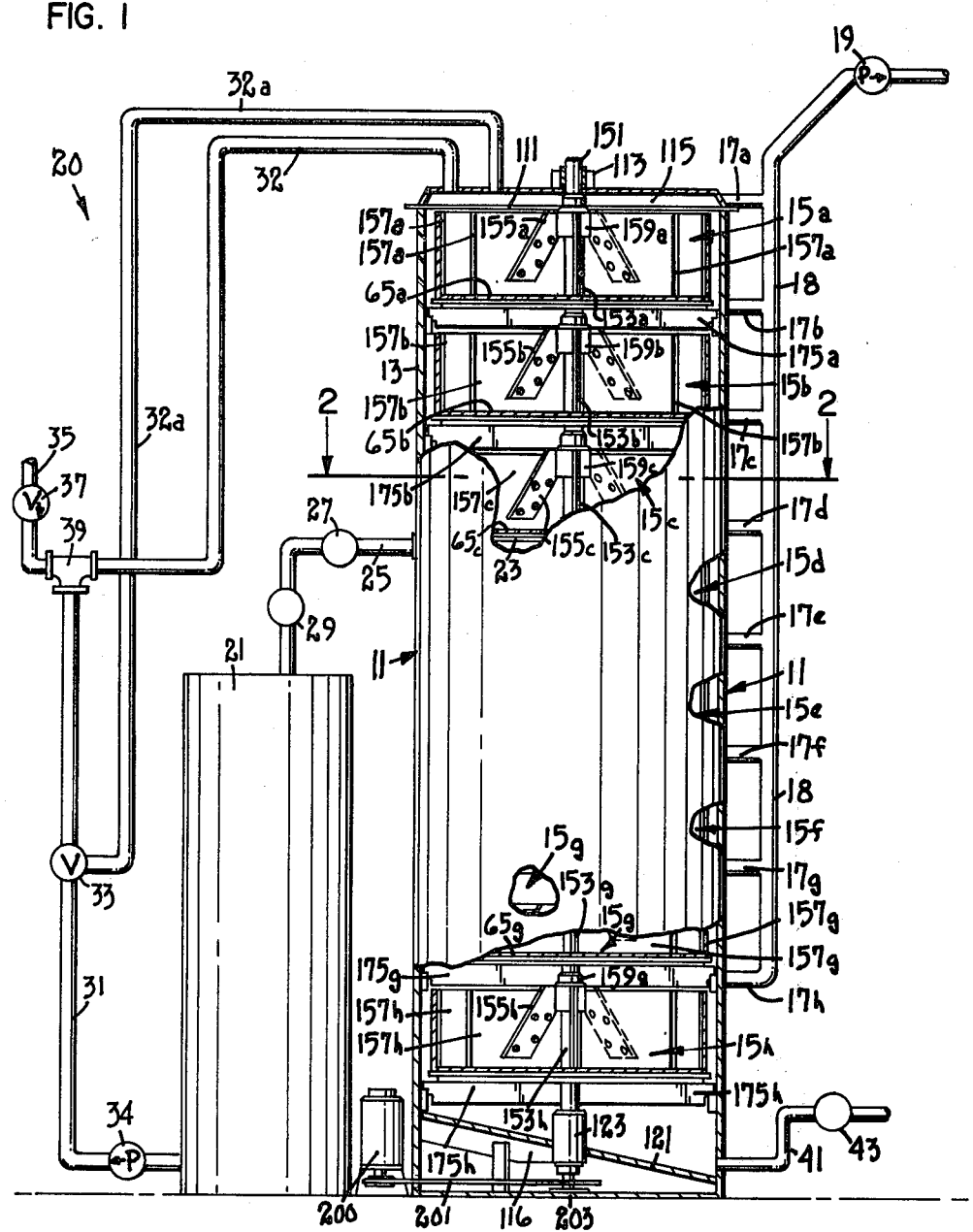
FIG. 1 is a side elevational view of a fermentation or conversion apparatus of this invention with parts broken away to show the internal structure of the fermentation tower.

As will be apparent from the foregoing discussion, the process of this invention can have a variety of uses generally related to industries such as alcoholic beverage manufacture and synthesis of solvents, fuels, pharmaceuticals, etc. A common thread running through processes of this invention is that a living inoculum is multiplied and brought to a high growth rate in the presence of a nutrient medium, and the products of the resulting live culture and/or the residues from the culture are the principal objectives of the microbiological synthesis. For purposes of illustration, the following description will be directed toward a continuous process for the production of useful metabolites from a carbohydrate-containing nutrient medium by fermentation of the medium, typical useful metabolites being one or more of the following: gaseous products such as carbon dioxide, oxygen-containing aliphatic liquids or solids such as lower ($C_1$ to $C_6$, preferably $C_2$-$C_5$) alkanols, carbonyl-containing compounds (aldehydes, ketones, and carboxylic acids), and more complex compounds such as riboflavin. The oxygen-containing aliphatic compounds can be polyfunctional but are typically monomeric in nature. A particularly preferred embodiment of this invention involves the conversion of a carbohydrate-containing material to a "beer" and a solid residue which, though depleted in carbohydrate, is substantially enhanced (percentage-wise) in protein. Indeed, because of the inclusion of dead cellular material in the residue, the protein level can be increased in an absolute sense as well.

A typical example of a fermentable feedstock useful in this invention is a starchy mash (potato mash, corn mash, or the like). When food supplies are under economic pressure, driving the cost of feed grains, legumes, tubers, etc. upward, a fermentable feedstock can be prepared from agricultural waste materials such as weeds, cornstalks, corncobs, and the like. Corn grain is reported to contain about 9% by weight of protein, a substantial portion of the balance of this grain being starch and other polysaccharides. Most animals (and humans as well) do not need such a high proportion of carbohydrate in their diet, and protein enrichment would normally be desirable for a diet heavily slanted toward corn grain, corn meal, or corn flour. In accordance with this invention, a substantial portion of the carbohydrate material in the corn grain is converted to useful organic liquids such as lower alkanols, with carbon dioxide being another useful by-product. The residual corn nutrient obtained from the process can contain 30% by weight of protein as opposed to 9%. Furthermore, this protein is typically in a more readily digestible form as compared to the corn grain starting material. In an absolute sense, 100 parts by weight of corn grain starting material contains 9 parts by weight of protein, but the ultimately obtained residue of fermentation can contain as much as about 10.5 parts by weight of protein, due to the presence of dead cellular material, e.g. dead yeast cells.

According to this preferred embodiment of the invention, suitable fermentable feedstocks are carbohydrate-containing, either in the form of material containing carbohydrate per se (e.g. sugars, starches, celluloses and hemi-celluloses, and other mono- and polysaccharides) or glycosides and the like, wherein a polysaccharide chain is linked to a non-carbohydrate nucleus. Some microorganism cultures (e.g. various well known species of the genus Clostridium) have the ability to utilize polysaccharides as a nutrient or substrate for fermentation. Typical yeasts, on the other hand, are more effective in fermenting monosaccharides such as glucose. Accordingly, an optional step of the process of this invention includes hydrolysis of the carbohydrate-containing feedstock. Starchy feedstocks such as corn mash can be hydrolyzed to sugars rather quickly with moderate heat and a catalyst such as an amylase or an organic or inorganic acid. Typically, the inoculum is then added to the hydrolyzed material, thereby providing a culture containing as its nutrient medium an aqueous solution of a naturally-occurring monosaccharide (glucose, fructose, mannose, galactose, gulose, similar aldohexoses and ketohexoses, ribose, or similar pentoses), their disaccharides, and their low molecular weight oligomers. Some unhydrolyzed starch may be dispersed in the nutrient medium, along with suspended cellulosic matter, proteinaceous matter, etc. Other by-products of the food and agricultural industries can provide a similar nutrient medium, typical of such by-products being molasses, whey, and other materials high in carbohydrate.

To provide conditions favoring fermentation, gaseous metabolites are typically removed from the growth zones or fermentation zones through a suction or degassing apparatus. This apparatus may also incidentally remove some water and organic liquids which are at least as volatilizable as water. The "beer" (water solution of organic liquids) removed from at least the lowermost of the growth or fermentation zones will typically contain the organic liquids, water, and dissolved and suspended residues from the nutrient medium. Various means for separating these components of the beer are well known in the art, including distillation, reverse osmosis, hyperfiltration, stripping, solvent extraction, settling, centrifugation, and various combinations of these techniques, including repetitions of substantially the same technique (e.g. fractional distillation followed by ternary azeotropic distillation). These separation steps can also bring about the concentration of organic liquids, e.g. the concentration of a 2–20% by volume alcoholic beer to at least about 40% by volume (about 80 U.S. proof), preferably 100–200 U.S. proof. Other known techniques useful in conjunction with this invention include the concentrating, liquefying, or solidifying of carbon dioxide; stripping and rectifying for the removal of non-potable or toxic or off-flavor chemicals such as aldehydes and ketones; and the like.

Figure 7:
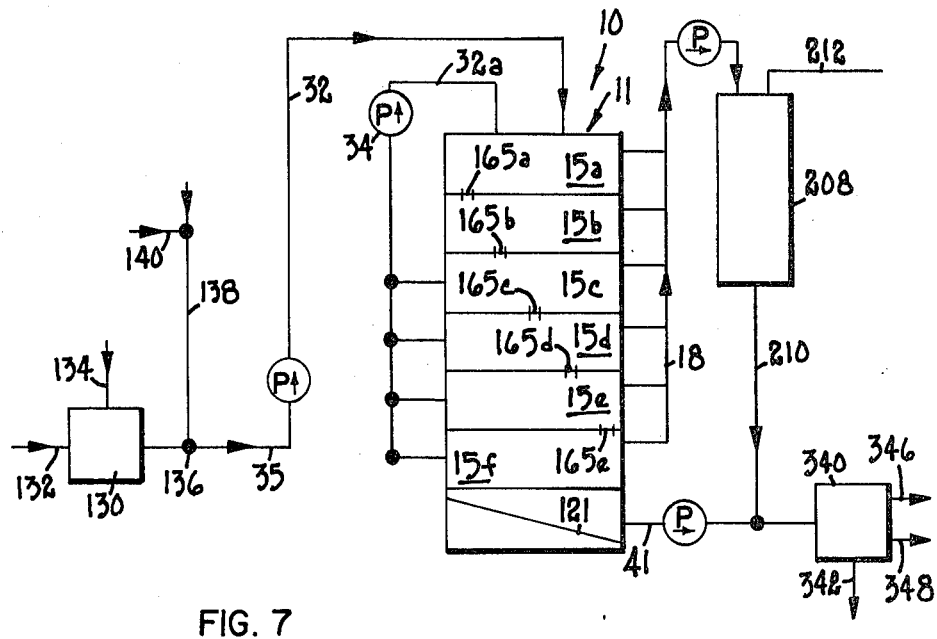
FIG. 7 is a schematic representation of a complete system for the production of liquid metabolites, gaseous metabolites, and high-protein solid residues, which system utilizes an embodiment of this invention.

For an overview of a typical system designed to carry out a preferred embodiment of a process of this invention (including some of the aforementioned optional steps), reference is made to FIG. 7. In this schematic representation, a mixture of finely ground starchy material suspended in water is introduced into a hydrolytic reactor 130 through supply line 132. A second supply line 134 is provided for the introduction of a catalytic agent for the hydrolysis (e.g. an acid or an amylase-containing medium). The output from reactor 130 is blended in-line at 136 with still another medium containing an inoculum, this medium being introduced through line 138. If the inoculum is a yeast, it will ordinarily be desirable to introduce air or oxygen through line 140 to stimulate yeast growth. Normally, line 140 will be the only means in the system for introducing air or oxygen, since substantially the entire fermentation process from feed line 35 onward is preferably conducted with the exclusion of the ambient atmosphere. If desired, however, specific gases ($O_2$, $CO_2$, etc.) can be deliberately introduced into tower 11. The culture flowing through feed line 35 is pumped through tower feed conduit 32 into the topmost fermentation or growth zone 15a in the tower-like production unit or fermentation tower 11. As will be explained in greater detail subsequently, fermentation tower 11 is divided into several such growth or fermentation zones; eight such zones are shown in FIG. 1 (described in more detail subsequently). For convenience of illustration, FIG. 7 shows only six such zones, but it will be understood that a greater or fewer number of zones can be included in fermentation tower 11. As noted previously, the flow of the culture or production medium from zone 15a to zone 15b to zone 15c, etc. is gravity-induced. The retention time in any given zone is a function of a number of factors, but it is preferred to make all zonal retention times generally equal. A typical retention time in each zone ranges from about one to 100 minutes, and a typical total elapsed time for the flow from tower feed conduit 32 to the tower bottom or catch trough 121 below the lowermost zone is only a few hours or less, e.g. one to 20 hours. However, the actual residence time in tower 11 is difficult to determine with precision, since the process of this invention involves recirculation of culture or production medium from lower zones to a higher zone, e.g. from zone 15c and lower to uppermost zone 15a. The recirculation system 20 is preferably designed to accomodate at least 10 or 20% of the total capacity of tower 11; more preferably, at least 40% of the total production medium in the fermentation apparatus is in the recirculation system 20, substantially the balance being in tower 11. One way of determining a residence time is to measure the influx through line 32 and the beer flow rate through line 41. To provide a complete material balance, the gases removed through degassing manifold 18 should also be taken into account. The culture tapped off into recirculation system 20 is pumped very gently to uppermost growth or fermentation zone 15a through conduit 32a. To avoid disrupting the logarithmic growth rate of the microorganisms in the culture, pump 34 exerts less than about one atmosphere (14.7 p.s.i.g.) gauge pressure, more typically less than about 0.2 atmospheres or less than about 20 kPa. It has been found that the culture (inoculum and nutrient medium) in the tower 11 and recirculation system 20 is well suited to gentle pumping and gravity flow. In the case of a fermentation with yeast, the culture contains a liquid nutrient medium. (It should be understood that the nutrient medium is considered a "liquid" even when it contains dispersed or suspended solid matter.) Liquid nutrient media such as a hydrolyzed mash (e.g. corn mash, potato mash, etc.) has a relatively low viscosity, not greatly different from the viscosity of water itself. Even the logarithmic growth of microorganisms in the culture does not so seriously increase the viscosity as to interfere with gravity flow and pumping. Furthermore, the constantly moving segments (described subsequently) in the growth or fermentation zones 15a, 15b, etc. help to provide agitation, generally uniform suspension or slurrying of solid, settlable matter and microorganism cells, and prevention of excess settling of material near the center or the periphery of fermentation or growth zones 15a, 15b, etc.

It is not necessary that all of the conduits feeding into recirculation system 20 (as shown in FIG. 7) be continuously open. When the process is optimized, a single feed from a single growth zone into recirculation system 20 may be sufficient, as illustrated in FIG. 1.

The recirculation system 20 brings a culture which is preferably in a logarithmic growth phase up to the topmost growth or fermentation zone 15a. This recirculation step accomplishes several objectives. It withdraws the rapidly growing culture from a lower zone of tower 11 before that culture approaches the termination phase too closely. It also brings the rapidly-growing culture into contact with fresh nutrient material, thereby partially making up for depletion of carbohydrate resulting from metabolic processes occurring in tower 11. It further inoculates zone 15a with rapidly multiplying microorganisms, so that the fresh culture introduced through tower feed conduit 32 is brought to the logarithmic growth phase relatively quickly.

Withdrawal of gaseous fermentation products (e.g. carbon dioxide) through degassing manifold 18 also helps to maintain growth and favor desired chemical reactions. The idealized chemical reaction for the early and middle stages of a carbohydrate fermentation with alcohol producing organisms is:

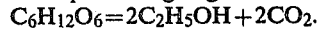
$$C_6H_{12}O_6 = 2C_2H_5OH + 2CO_2.$$

Under accepted principles of chemistry, removal of the carbon dioxide should shift the equilibrium to the right. Near the end of the fermentation, more complex reactions are likely to occur, wherein, among other things, acetic acid and glycerine as well as carbon dioxide and ethanol can be formed.

According to the scientific literature, a weight ratio of at least 1:1 solid nutrient material: yeast will permit yeast growth. Maintenance of the logarithmic growth phase, however, may require a considerably higher ratio, e.g. 6:1 nutrient:yeast. These ratios assume a nutrient consisting essentially of monosaccharides, with sufficient phosphates, nitrogen-containing compounds, and the like to support yeast growth. In this invention, the incoming inoculum will typically be provided with a large excess of nutrient material. The culture in the recirculation system 20, on the other hand, will tend to be at or near the ratio favoring the most rapid growth of yeast organisms. By combining the flow from the recirculation system and the incoming flow through tower feed conduit 32, a healthy, rapidly multiplying yeast culture is quickly resupplied with nutrients, while the fresh incoming culture is bolstered in microorganism population so as to speed up the metabolism of the incoming nutrient material and thereby reduce retention time or residence time in tower 11. In other words, the upper growth or fermentation zones are not allowed to get too high in nutrient:yeast ratio (e.g. not too far beyond 6:1), while the lower zones are not allowed to get too low in this ratio (e.g. below 1:1 nutrient:yeast).

The gases withdrawn through degassing manifold 18 are conveyed to a condenser 208, which condenses any organic liquids and water volatilized by the degassing system. The condensed liquids pass through line 210 so that they can be combined with the beer withdrawn from the bottom of the tower 11 through beer conduit 41. The resulting combination of liquids, nutrient residues, etc. is conveyed to a separation zone 340, which can utilize the principles of distillation, hyperfiltration, reverse osmosis, solvent extraction, rectification, stripping, or any other desired prior art technique for liquid/liquid or liquid/solid separation. As a result of this separation or series of separations, volatilizable metabolites are isolated and concentrated and flow out through line 346, while solid residues (protein-enriched mash or the like) flow out through line 342. Water removed from the beer and the nutrient medium flows out through line 348 and can be discarded or reused in the process. Suitable separation or concentration equipment can be obtained from commercial suppliers or custom built according to principles well known and well understood in the arts of distillation, solvent extraction, stripping, vacuum evaporation, reverse osmosis, and the like. For example, a conventional distillation column will suffice for the manufacture of 100 to 190 U.S. proof fuel alcohol. The conversion of such fuel alcohol to absolute alcohol (e.g. for use in making "gasohol", which is 90% gasoline/10% alcohol, or for solvent use) can be carried out by any conventional technique including ternary azeotropic distillation with benzene, straight-run gasoline, or other unleaded hydrocarbon mixtures. Such additional conversions are entirely optional, insofar as the present invention is concerned, particularly in view of the fact that various types of heat engines, space heaters, and the like can be designed to run on almost any organic liquid solution which is combustible and hence a "fuel". Even internal combustion engines can be run on fuels containing up to about 30% by volume of water.

The Preferred Growth-Stimulation or Fermentation Apparatus

FIGS. 1 through 6 of the Drawing illustrate a preferred apparatus suitable for carrying out the process of this invention. For illustrative purposes, it will be assumed that the apparatus shown in FIGS. 1 through 6 is a continuous fermentation apparatus for continuously fermenting a continuously-supplied stream of fermentable feedstock.

Turning first to FIGS. 1 through 4, with particular emphasis on FIG. 1, the continuous fermentation apparatus 10 comprises principally the fermentation tower 11 and the recirculation system 20.

The recirculation system 20 includes a collection means, in this case a collection trough 23 positioned a little less than half-way down the length of the tower 11 (also referred to hereinafter as a fermentation tower). In the embodiment shown in FIG. 1, only one such collection means 23 (shown in phantom) has been provided. Additional collection means can be provided, as shown in FIG. 7. Ordinarily, a single collection means 23 is adequate to keep a substantial portion of the total fermentation medium in apparatus 10 continuously flowing through the recirculation system 20. However, for any given substrate or feedstock, there will be an optimum location for collection means 23. For some substrates and some conditions or desired products, location of the collection means closer to the top of the tower 11 would be more appropriate, for other substrates, conditions, or products, a location closer to or at the bottom would provide better results. Collection means 23 (see also FIG. 4) conveys partially fermented material through conduit 25 and valve 27 and check valve 29 to recirculation reservoir 21, which has a capacity approximately equal to four fermentation or growth zones, e.g. 15a, 15b, 15c, and 15d, generally referred to hereinafter as fermentation zones. The material in reservoir 21 can pass through recirculation feed conduit 31 and valve 33 to mixing tee 39 for in-line mixing with raw feed from conduit 35 (and check valve 37). In any event, mixing tee 39 communicates with the tower feed means 32. Alternatively, valve 33 can be used to bypass mixing tee 39 via bypass conduit 32a, which communicates directly with the uppermost fermentation zone 15a. See also FIG. 7, wherein this alternate route is represented schematically. The use of bypass 32a is preferred for sensitive microorganism cultures, e.g. yeasts, a preferred yeast being conventional brewer's yeast or "bottom yeast". The entire recirculation and feed system is preferably as water-tight and air-tight as is reasonably practical under the circumstances. If the fermentation apparatus 10 needs to be provided with a source of oxygen for microorganisms or the like which multiply more rapidly under aerobic conditions, air or oxygen can be introduced upstream of tower feed conduit 32 (as shown in FIG. 7), with the objective of optimizing organic liquid production in tower 11. Alternatively, as noted previously, one can deliberately introduce various gases ($O_2$, $CO_2$, etc.) into tower 11 to stimulate or suppress various types of chemical or biological action.

Fermentation tower 11 includes an outer shell 13 (FIGS. 1 through 4) which defines a generally vertically extending space, which is sufficiently elongated to allow for the stacking or vertical arrangement of a plurality of tray-like fermentation zones 15a, 15b, 15c, etc. Again, the nature of the substrate or feedstock, the nature of the fermentation conditions, the desired products, the desired retention time, and so forth will determine the optimum number of tray-like fermentation zones 15a, 15b, etc. In order to produce a beer containing more than 2% by volume of organic liquid fermentation products in a reasonable time, at least three tray-like fermentation zones (15a through 15c) would ordinarily be preferred. So that the energy requirements for concentrating the beer will not be too unattractive economically, at least six tray-like fermentation zones (15a through 15f) would be continuously operating in a tower constructed according to this invention. The particular tower 11 shown in FIG. 1 has eight such tray-like fermentation zones (15a through 15h), but it will be understood that even more zones can be utilized, depending upon the factors described previously. In the preferred operation of this invention, the retention time in the topmost tray-like fermentation zone 15a is within the range of 5 to 100 minutes, depending upon the speed of rotation of the movable segments within the zone. In the production of fuel alcohol from a mash (corn mash, potato mash, etc.), 10 to 20 minutes would be a more typical retention time. Since, for the sake of simplicity, the rate of rotational movement in each of the additional tray-like fermentation zones (15b through 15h) is the same as that of the topmost zone 15a, a typical flow time from the topmost zone 15a to the inner bottom plate 121 is 80 to 160 minutes, with a substantial portion of the discharge or gravity flow from fermentation zone 15c (30 to 60 minutes down the tower) being withdrawn or tapped off into the recirculation system 20.

Although a pump 34 is used to raise the mixture emerging from mixing tee 39 to the top of tower 11, no pumping is required within the tower 11, and all zone-to-zone movement of fermentation medium is substantially a gravity flow. Indeed, tower feed conduit 32 preferably communicates with the interior space above tray-like fermentation zone 15a, so that gravity flow begins as the feed from conduit 32 enters the upper end of the space defined by shell 13 of tower 11. In this preferred configuration, tower feed conduit 32 passes through top plate 111 of outer shell 13 in a fluid-tight manner. As noted previously, tray-like fermentation zone 15a is divided into movable segments by means of movable partitions or divider vanes or paddles 157a. These partitions 157a rotate about the longitudinal axis of the fermentation tower 11. (Tower 11, its cylindrical outer shell 13, and tray-like fermentation zones 15a through 15h are all cylindrical and concentric with this longitudinal axis.) In the preferred embodiment shown in the Drawing, partitions 157a rotate, while the generally horizontal floor 65a and the vertically extending cylindrical wall 55a of fermentation zone 15a remain stationary. Despite the movement of partitions 157a with respect to the stationary wall 55a and floor 65a, substantially fluid-tight segmentation of zone 15a can be provided by techniques known in the art. Alternatively (but less preferably from the standpoint of convenience of manufacture), partitions 157a, wall 55a, and floor 65a can be a single, integral structure. In this alternative embodiment of a tray-like fermentation zone (not shown), each segment of the tray preferably contains its own drain or discharge opening which is normally closed except for the period of time needed to discharge its contents into the next lower tray at the conclusion of a tray revolution. In the preferred embodiment shown, however, all drain openings are fixed and constantly open. Relocation or rearrangement of drain openings can be provided by removing individual tray-like fermentation zones 15a through 15h and re-inserting them in the tower 11 in different drain opening locations with respect to each other. In the ordinary practice of this invention, however, the location of drain openings would not have to be changed. In the normal practice of this invention, tower feed conduit 32 feeds into that segment of the tray-like fermentation zone 15a which is, at the time it receives the feed, substantially empty and at least three-fourths of a revolution away from the drain opening. The manner in which the segments operate to retain fermentation medium for a controlled period of time will be explained in greater detail in connection with the description of FIGS. 2, 3, 4, and 6.

FIGS. 2-4 and 6 illustrate the operation of the fermentation zone 15c, which receives the discharge or gravity feed or flow from fermentation zone 15b, zone 15b being in turn fed by fermentation zone 15a. This third fermentation zone 15c is selected to illustrate the operation of all tray-like fermentation zones 15a through 15h, since these zones operate in substantially the same manner. In addition, zone 15c illustrates the use of the collection means 23 to tap off a substantial portion of the gravity flow from zone 15c for recirculation through recirculation system 20 to bypass 32a or to mixing tee 39 and tower feed conduit 32. As will be apparent from FIGS. 2 through 4, tray-like fermentation zone 15c l is divided into eight segments by movable partitions 157c. Movable partitions 157c all radiate outward from the center of zone 15c. They are rotatable and are rotated by means of paddle arms 155c. Paddle arms 155c are attached to paddles 157c by threaded fastening members 255c. Of course, a variety of means could be used to fasten paddle arms 155c to paddles 157c, but threaded members 255c are convenient, since they permit easier assembly and disassembly of the apparatus. For example, it may be convenient to assemble apparatus 10 "in plant" (i.e. at the production site). Such in-plant assembly can be carried out conveniently by inserting the tray-like fermentation zones 15a through 15h into shell 13 one at a time, with drive shaft 151 in place and with each set of paddles (beginning with paddles 157h) dropped down onto each tray-like fermentation zone (beginning with 15h) and attached to the drive shaft through a linkage including the paddle arms (starting with 155h) and other elements which will now be described.

Figure 3:
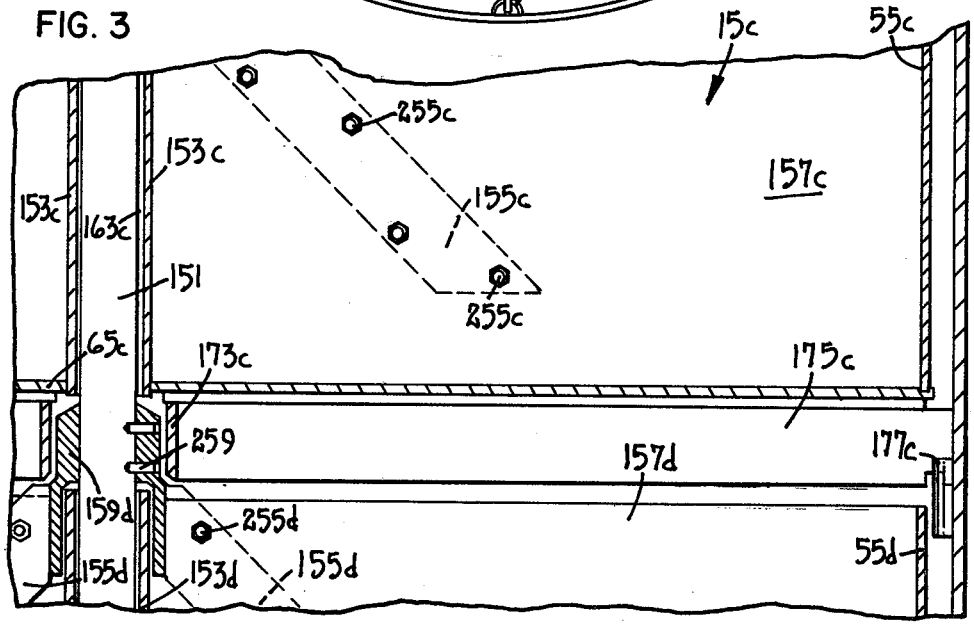
FIG. 3 is a cross-sectional view, taken along line 3—3 of FIG. 2.

In the case of zone 15d, as in the other fermentation zones, paddle arm 155d is integral with a hub 159d which snuggly engages drive shaft 151 and is attached thereto with pins 259 (FIG. 3). Thus, when tray-like fermentation zone 15d and its movable segments are fully assembled, paddles 157d are integral with the paddle arm/hub assembly 155d/159d which is connected to drive shaft 151 at hub 159d. As noted previously, these elements can all be disassembled to permit removal of the movable segments for cleaning, repair, and the like.

The lower end (approximately the lower half) of hub 159d surrounds and encloses a cylindrical vertical sleeve 153d as shown in FIGS. 3 and 4. Sleeve 153c (FIG. 3) coincides with and defines the central opening 163c in the floor 65c of fermentation zone 15c. This opening 163c and the vertically-extending sleeve 153c which occupies the opening, and openings and sleeves above and below it in overlying and underlying fermentation zones (sleeve 153b of zone 15b, sleeve 153d of zone 15d, etc., best illustrated in FIG. 6) define a generally vertically extending shaft tunnel for drive shaft 151. In addition, sleeve 153c imparts structural integrity to tray-like fermentation zone 15c while defining, in effect, the inner wall of the doughnut-shaped or toroidal zone defined by sleeve 153c in combination with the outer wall 55c. In short, tray-like fermentation zone 15c is preferably a generally verticaly-extending toroidal space closed off at its lower end by floor 65c, which floor 65c is a two-dimensional torus. As will be most apparent from FIG. 4, the top edge of paddles 157c is just below the top edge of wall 55c. In operation, the upper or free surface of the fluid fermentation medium in zone 15c preferably is no higher than the topmost edge of paddles 157c and is optimally slightly lower.

Figure 2:
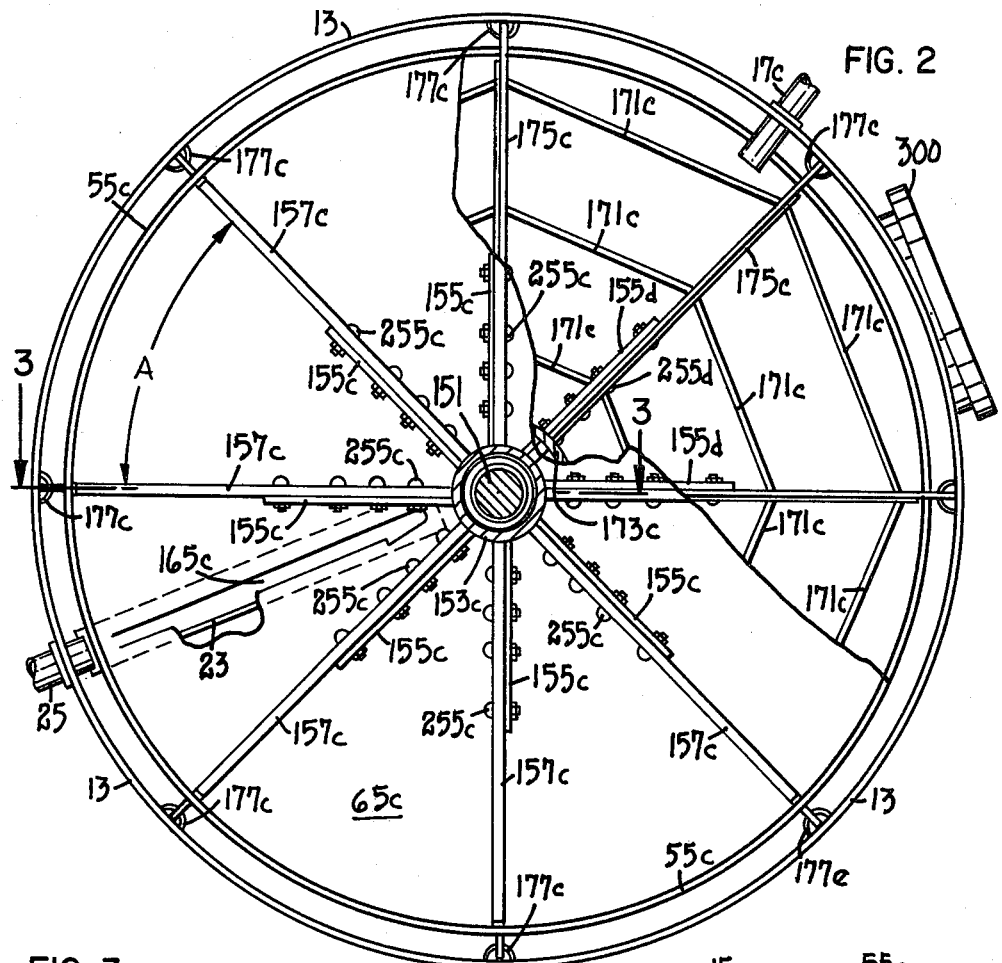
FIG. 2 is a cross-sectional view taken along line 2—2 of FIG. 1.

As shown in FIGS. 2 and 4, each adjacent pair of paddles 157c, in combination with the subtended portion of wall 55c and sleeve 153c defines a movable segment having an angle or circumferential portion A. In the preferred embodiment shown, angle A is 45°. For efficiency of operation in a reasonable number of fermentation zones, angle A would normally not exceed 180° and typically be not more than 90°. On the other hand, the complexity of the structure of fermentation zone 15c might be greatly increased if angle A were less than 45°. Although many of the elements of fermentation zone 15c can be constructed from relatively lightweight plastics such as polyolefins (even "high density" polyethylene has a specific gravity less than 1.0), at least some of the elements in the zone (e.g. hub 159c) may be constructed of metal (e.g. stainless steel) and, in any event, the total weight of zone 15c filled nearly to the brim with a fermentation medium weighing at least about one kilogram per liter will be extremely heavy and require an adequate support structure. This support structure is illustrated in FIG. 2, wherein a portion of floor 65c has been broken away to show support ribs 175c, extending radially outward from support ring 173c. Braces 171c tie together and radial ribs 175c in a chord-like concentric arrangement which provides additional structural strength. Each radial rib 175c is designed to engage a hanger 177c, much in the manner of a key fitting into a key-way. This rib/hanger engagement fixes the tray-like fermentation zone 15c in the desired position but also permits removal of the tray-like zone 15c, e.g. by hoisting the zone 15c directly upward.

The centrally-located support ring 173c is in register with sleeve 153c and thus also forms a part of the shaft tunnel through which drive shaft 151 runs. As shown in FIG. 3 and FIG. 2, the inside diameter of support ring 173c is slightly larger than the outside diameter of sleeve 153c or even the lower half of hub 159c.

As best shown in FIG. 4, there is sufficient space above the upper edge of wall 55c to allow for communication with suction or degassing conduit or tube 17c, which removes gaseous fermentation products (e.g. carbon dioxide) from fermentation zone 15c and conveys these gaseous products to the suction or degassing manifold 18. There is also sufficient space below floor 65c of zone 15c and above the upper edge of wall 55d to allow for the placement of trough 23, which collects a substantial portion of the downward flow from zone 15c and conveys it, through conduit 25 and valve 27 to the recirculation system 20 (FIG. 1). As best shown in FIG. 2, the elongated drain opening 165c in floor 65c is located immediately above trough 23, so that much of the fermentation medium draining through drain opening 165c will fall into trough 23. Drain opening 165c is substantially, but not exactly, radially oriented with respect to the center of floor 65c. Thus, drain opening 165c is offset from but generally parallel and in closely spaced relation to a radius extending from the center of floor 65c, i.e. from the generally vertical axis of fermentation tower 11. By means of this slight offsetting of drain opening 165c, a clockwise motion of paddle 157c will result in exposure of the end of drain opening 165c which is located closest to the center of floor 65c. When the fermentation medium within fermentation zone 15c has a very low viscosity (e.g. a viscosity in the hundreds of centipoise or less), a large amount of the fermentation medium within the moving segment approaching drain opening 165c will drain out as soon as paddle 157c has crossed over the end of opening 165c adjacent the center of floor 65c. For a high viscosity fermentation medium, a drain opening which is exactly radially oriented might be preferable. However, it has been found that the viscosity of, for example, a corn mash mixed with water is not very different from water itself. (Apparently, the tiny particles of corn mash do not have a thixotropic effect with respect to the aqueous phase of the fermentation medium.)

It may be desirable to observe the operation of the interior of fermentation tower 11, and a sealed porthole 300 (FIG. 2) provided with a glass or plastic lens (not visible in FIG. 2) is included in the structure of shell 13 for this purpose. An additional advantage of porthole 300 is that further conduits, troughs, or the like can be inserted into the interior of fermentation tower 11 using suitable peripheral sealing collars or the like (not shown), thereby avoiding the necessity or cutting through shell 13 if such additional elements become desirable after the construction of tower 11 is complete.

As noted previously, it is ordinarily desirable to exclude the ambient atmosphere from the interior of tower 11, even when the fermentation processes taking place within tower 11 are not exclusively anaerobic. Furthermore, it is desirable that the interior of tower 11 be under subatmospheric pressure to assist in the degassing via suction tubes or conduits 17a–17h and manifold 18. Yet, in the embodiment shown, drive shaft 151 extends along the entire vertical axis of tower 11 and is driven by a motor 200 and chain drive means 201 located outside of the sealed subatmospheric interior space defined by shell 13 of tower 11. For convenience of illustration, the motor 200 and the chain drive 201 are shown at the bottom of tower 11. In actual practice, it may be convenient to drive the drive shaft 151 from at its top end. To provide bearings for drive shaft 151 and to prevent leakage of ambient air into the aforementioned sealed inner space, seal and bearing housings 113 and 123 (FIGS. 1 and 5) are included within the structure of tower 11.

Turning to FIG. 5, top seal and bearing housing 113 is a substantially cylindrical projection extending upwardly from top plate 111. Reinforcing rib 115 also extends upwardly from top plate 111 and radially outward from housing 113. Housing 113 is provided with a seal 119 which prevents leakage of ambient air into the interior of tower 11 by sealingly engaging the outer surface of drive shaft 151. This sealing engagement does not prevent rotation of drive shaft 151, however. The upper end of drive shaft 151 is held in the desired orientation by bearing 117, which also permits rotation of drive shaft 151.

FIG. 5 also illustrates the structure of bottom seal and bearing housing 123, which is similar in design and in concept to the top housing 113. The bottom seal and bearing housing 123 extends both upwardly and downwardly from inner bottom plate 121. Above plate 121, the vacuum and ambient air exclusion conditions are maintained. Providing these conditions above bottom plate 121 is desirable, since, while only a very minor amount of fermentation (if any) may be taking place in the space immediately above plate 121, this plate 121 nevertheless serves as a catch trough for the discharge from lowermost fermentation zone 15h (FIG. 1). Bottom plate 121 is slanted downwardly so as to direct the flow of the beer into a suitable withdrawing means, in this case beer conduit 41. (The beer is pumped by pump 43 to a conventional apparatus for further processing of the beer, including concentration of the organic liquids in the beer; see FIG. 1.)

Returning to FIG. 5, housing 123 is provided with bottom seal 129 and bottom bearing 127, which are similar in design to top seal 119 and top bearing 117. As noted previously, the drive means for drive shaft 151 (i.e. motor 200 and drive chain 201) can therefore be located outside of the sealed interior of tower 11. Drive chain 201 can engage the lower end of drive shaft 151 by any suitable means such as the sprocket 203 shown in FIG. 1. To provide additional support for the tower structure, a brace or rib 116 radiates from the outer surface of housing 123 out to the inside surface of shell 13.

It will be understood that the foregoing description of the tower, the recirculation/feed system, the degassing system, and the beer withdrawal system is merely illustrative, and modifications can be made to better accomodate and process various feedstocks, fermentation products, and the like. For example, if the enzymes catalyzing the conversion of the feedstock produce primarily gaseous products such as methane or $CO_2$ rather than liquid fermentation products, withdrawing means 41 can be for removing suspending or dispensed residues only while manifold 18 can be for removing the gaseous metabolites.

Operation of the Apparatus

The incoming mash or other fermentable feedstock is preferably blended with an active microorganism culture before passing through check valve 37. Partially fermented material and the highly active, rapidly growing culture are preferably conveyed to the first tray-like fermentation zone 15a via bypass 32a, while the flow from valve 37 is conveyed to zone 15a through conveying means or conduit 32. The gravity feed from conduits 32 and 32a falls into a movable segment of zone 15a defined by a pair of adjacent paddles 157a. This segment rotates through almost a full revolution before reaching the drain opening and discharging into zone 15b. A similar sequence of events occurs in zone 15b and the fermentation medium then drops through the drain in zone 15b into the movable segment just "beyond" drain opening 165c in zone 15c. This movable segment describes about ⅞ of a revolution (about 315°) before its leading paddle 157c reaches drain opening 165c, from which the fermentation medium drains, partly into zone 15d and partly into trough 23. The material in trough 23 exits through shell 13 via conduit 25 and into the recirculation system 20, from which it flows via bypass 32a to tower 11, to begin a new pass through zones 15a, 15b, etc., starting with zone 15a. The material collected in trough 23 contains a vastly multiplied microorganism culture. The short, at least the first three fermentation zones 15a, 15b, and 15c provide fermentation, agitation, and organism multiplication in this preferred mode of operation, thereby providing a high ratio of active microorganisms to fermentable material.

The fermentation medium in zone 15d continues to rotate and flow downward through zones 15e, 15f, 15g, and 15h of tower 11 until it is discharged from the lowermost zone 15h onto inner bottom plate 121, which acts as a catch trough feeding the beer conduit 41. The location of drain openings 165a, 165b, etc. is illustrated in FIG. 6.

Assuming for the sake of illustration that the drain opening in zone 15a is generally at 270° of the circle of rotation of drive shaft 151, and assuming a clockwise rotation of drive shaft 151 from 270° through 315°, 360°, 45°, 90°, 135°, etc., the fixed drain openings (165b, 165c, 165d, etc.) will be located as follows with respect to 270° in zone 15a: 165b (FIG. 6) at 225°, 165c at 180° (FIG. 6), 165d (FIG. 6) at 135°, 165e (not shown) at 90°, 165f (not shown) at 45°, 165g (not shown) at 0°, and 165h (not shown) at 315°. As will be apparent from FIG. 6, the clockwise-rotating segment in zone 15b which has just passed 225° will receive a gravity feed from zone 15a. This segment will then be out of register with the drain opening and will pass through 360° and all the way around to 225° before coming into register and discharging into zone 15c. (In other words, the material discharged into zone 15b is retained from about ⅞ of a full revolution of drive shaft 151.) The segment of zone 15c receiving the discharge from zone 15b will have just passed 180°, i.e. just "beyond" opening 165c, and will have to pass through 360° and around to 180° before reaching the portion of floor 65c which has opening 165c. The material retained in this segment will then drain out into trough 23 and zone 15d. The segment of zone 15d receiving the discharge will have just passed 135° and will have to rotate about ⅞ of a revolution to reach the drain opening. The sequence of events in zone 15d is repeated for zones 15e, 15f, 15g, and 15h, as indicated previously.

The beer withdrawn from the inner bottom plate 121 will typically be a water solution containing, for example, about 3–20% by weight of ethyl alcohol and relatively smaller amounts of acetaldehyde, acetone, acetic acid, and fusel oil. Preferably, the vacuum within the shell 13 is continuously maintained, the feedstock continuously introduced through conduit 32, and the beer continuously withdrawn through conduit 41. Because of the effect of recirculation system 20, at least some of any live culture in apparatus 10 can be continuously recirculated to increase its hardness and efficiency; the balance of the culture will typically become part of the "bottoms" or solid residue of the process, as explained earlier.

Although a brewer's yeast/carbohydrate medium is the preferred culture or production medium, other cultures are suitable, particularly those which secrete a carbohydrase enzyme (zymase, glucase, cellobiase, cellulase, amylase, lactase, sucrase, or similar carbohydrases). Various isomerases, hydrolases, proteases, lipases, etc. are also provided by live cultures known in the art. The presently preferred metabolic product of the yeast/carbohydrate medium or culture is 100–190 U.S. proof fuel alcohol, which can be made anhydrous if desired.

For large-scale production of a tower 11 of this invention, it is desirable to simplify the design of the interior of the tower. For example, the upwardly-extending cylindrical walls 55a, 55b, 55c, etc. of zones 15a, 15b, 15c, etc. can be nonintegral with the zone floors 65a, 65b, etc., but integral with outer shell 13—or even eliminated entirely, whereby the upwardly-extending cylindrical walls 55a, 55b, etc. for each zone 15a, 15b, etc. can be the interior surface of shell 13 itself. In this embodiment (not shown), each floor 65a, 65b, 65c, etc. is provided with a peripheral sealing member (e.g. a rubbery element) which sealingly engages the interior surface of shell 13. With the proper fluid-tight sealing engagement of interior of shell 13 and the periphery of each floor 65a, 65b, etc., the support structure for each floor can be provided in a manner substantially similar to that shown in FIG. 2 Drawing, i.e. radial ribs 175, hangers 177, braces 171, and support ring 173. This large-scale production embodiment is also advantageous when manufacturing the entire interior of tower 11 out of stainless steel (for use in making food-grade products).

What is claimed is:

1. A process for stimulating the growth of a microorganism culture in a series of growth zones and withdrawing metabolites produced by said culture from a said growth zone, said process comprising the steps of:
    (a) introducing a microorganism culture comprising an inoculum and a liquid nutrient medium to the upper end of a tower-like production unit divided into a generally vertical series of tray-like growth zones, whereby said culture is introduced by the uppermost of said tray-like growth zones, each said growth zone having a drain opening and being subdivided into substantially liquid-tight, continuously moving, movable segments for continuously agitating the thus-introduced culture in said zone and for advancing said culture toward said drain opening;
    (b) advancing in a said movable segment, said culture toward said drain opening in said uppermost of said tray-like growth zones;
    (c) obtaining gravity flow of said culture through said drain opening into a movable segment of the next lowest or next-to-uppermost of said tray-like growth zones;

(d) repeating said steps (b) and (c) in said next-to-uppermost of said tray-like growth zones, thereby obtaining gravity flow to a movable segment of the next lowest tray-like growth zone below said next-to-uppermost of said tray-like growth zones;

(e) further repeating said steps (b) and (c) in successively lower tray-like growth zones until substantial multiplication of the microorganisms in said culture has been obtained;

(f) withdrawing a portion of said culture from a said tray-like growth zone and circulating the thus-withdrawn portion to a higher tray-like growth zone; and (g) withdrawing said metabolites from at least one of said tray-like growth zones.

2. A process according to claim 1 wherein said liquid nutrient medium comprises a material selected from a group consisting of a carbohydrate and a glycoside; said material is metabolized by the microorganisms in said culture, the metabolic process of said microorganisms being fermentive in nature; and said metabolites withdrawn according to said step (g) are concentrated and recovered.

3. A process according to claim 1 wherein each said growth zone is generally cylindrical and is divided into substantially fluid-tight, continuous moving, movable segments of less than 180° each.

4. A continous process for the production of useful metabolites from a carbohydrate-containing nutrient medium by fermentation of said medium, said process comprising the steps of:

(a) continously introducing a microorganism culture comprising a inoculum and said nutrient medium to the upper end of a tower-like fermentor sealed off from the ambient atmosphere and divided into a vertical series of generally cylindrical fermentation zones arranged generally vertically along the vertical axis of said tower-like fermentor, each said fermentation zone being divided into substantially liquid-tight, continously rotating segments, whereby said culture is initially introduced into a continuously rotating segment of the first and uppermost of said fermentation zones;

(b) continuously rotating said continuously rotating segment at least about three-fourths of a revolution to a gravity flow transfer means for transferring the culture to the second and next-to-uppermost of said fermentation zones, the retention time in a higher fermentation zone ranging from about 1 to about 100 minutes;

(c) continuously transferring said culture by gravity flow to a continuously rotating segment of the said second and next-to-uppermost of said fermentation zones, the retention time in said next-to-uppermost of said fermentation zones being generally equal to the retention time in said uppermost fermentation zone;

(d) continuing the transfer of said culture by gravity flow to continuously rotating segments of successively lower fermentation zones at least until such culture is in a logarithmic growth phase;

(e) continuously withdrawing a portion of the culture in the logarithmic growth phase from a said lower fermentation zone before the concentration of metabolites in the culture reaches a level high enough to stop growth of the culture, and pumping the thus-withdrawn portion at a gauge pressure below about one atmosphere to said first and uppermost fermentation zone without exposing said thus-withdrawn portion to the ambient atmosphere or to contamination with extraneous microorganisms;

(f) withdrawing metabolites from at least the lowest of said fermentation zones without exposure of said zone to the ambient atmosphere or to contamination with extraneous microorganisms; and (g) recovering useful metabolites from the thus-withdrawn metabolites.

5. A process according to claim 3 wherein each fermentation zone is divided into substantially fluid-tight, continuously rotating segments of less than 90° each, and each fermentation zone is constantly draining liquid medium from a constantly open drain opening.

6. A process according to claim 4 wherein said microorganism culture comprises brewer's yeast and a hydrolyzed starch-containing aqueous nutrient medium.

7. A process according to claim 4 wherein the thus-withdrawn metabolites include a lower alkanol and carbon dioxide.

8. A process according to claim 7 wherein a beer containing a lower alkanol is withdrawn from the lower end of said tower-like fermentor, a lower alkanol in said beer is concentrated to at least about 40% by volume, and residual nutrient medium is recovered from said beer.

9. A process according to claim 7 wherein said continuously rotating segments rotate at the rate of about 0.01 to about 0.2 revolutions per minute.

10. A process according to claim 7 wherein the interior of said tower-like fermentor is under subatmospheric pressure, and carbon dioxide is withdrawn from each said fermentation zone in gaseous form.

11. A process for stimulating the growth of a microorganism culture in a series of growth zones and withdrawing metabolites produced by said culture from a said growth zone, said process comprising the steps of:

(a) introducing a microorganism culture comprising an inoculum and a liquid nutrient medium to the upper end of a tower-like production unit divided into a generally vertical series of tray-like growth zones, whereby said culture is introduced to the uppermost of said tray-like growth zones, each said growth zone having a drain opening and being subdivided into substantially liquid-tight, continuously moving, movable segments for continuously agitating the thus-introduced culture in said zone and for advancing said culture toward said drain opening;

(b) advancing in a said movable segment, said culture toward said drain opening in said uppermost of said tray-like growth zones;

(c) obtaining gravity flow of said culture through said drain opening into a movable segment of the next lowest or next-to-uppermost of said tray-like growth zones;

(d) repeating said steps (b) and (c) in said next-to-uppermost of said tray-like growth zones, thereby obtaining gravity flow to a movable segment of the next lowest tray-like growth zone below said next-to-uppermost of said tray-like growth zones;

(e) further repeating said steps (b) and (c) in successively lower tray-like growth zones until substantial multiplication of the microorganisms in said culture has been obtained;

(f) withdrawing a portion of said culture from a said tray-like growth zone;

(g) withdrawing said metabolites from at least one of said tray-like growth zones; and (h) introducing partly metabolized nutrient material and microorganism cultures in a logarithmic growth phase into a higher tray-like growth zone, thereby increasing the ratio of live, mature, rapidly growing, metabolite-tolerant microorganisms to nutrient material in said higher tray-like growth zone and shortening any lag time in said growth zone.

12. A process according to claim 11 wherein the ratio of nutrient material to microorganism culture in all of said tray-like growth zones is maintained within the range of about 1:1 to about 6:1.

13. A process according to claim 11 wherein each said growth zone is generally cylindrical and is divided into substantially fluid-tight, continuous moving, movable segments of less than 180° each.

* * * * *